(12) United States Patent
Zhang

(10) Patent No.: US 9,986,980 B2
(45) Date of Patent: Jun. 5, 2018

(54) BIOLOGICAL SAMPLE PRESERVATION TUBE WITH IDENTIFICATION CODE AND METHOD FOR MANUFACTURING THE SAME

(71) Applicant: Hangzhou Biobank Biotech Inc., Hangzhou (CN)

(72) Inventor: Yang Zhang, Hangzhou (CN)

(73) Assignee: HANGZHOU BIOBANK BIOTECH INC., Hangzhou (CN)

( * ) Notice: Subject to any disclaimer, the term of this patent is extended or adjusted under 35 U.S.C. 154(b) by 67 days.

(21) Appl. No.: 15/131,928

(22) Filed: Apr. 18, 2016

(65) Prior Publication Data

US 2016/0228103 A1 Aug. 11, 2016

Related U.S. Application Data

(63) Continuation of application No. PCT/CN2014/082870, filed on Jul. 24, 2014.

(30) Foreign Application Priority Data

Oct. 18, 2013 (CN) .......................... 2013 1 0487889

(51) Int. Cl.
*B01L 3/14* (2006.01)
*B29C 45/14* (2006.01)
(Continued)

(52) U.S. Cl.
CPC ........ *A61B 10/0096* (2013.01); *B01L 3/5453* (2013.01); *B29C 45/14* (2013.01);
(Continued)

(58) Field of Classification Search
None
See application file for complete search history.

(56) References Cited

U.S. PATENT DOCUMENTS

2003/0067099 A1* 4/2003 Miller ............... B29C 45/14811
264/447
2011/0308335 A1* 12/2011 Pink ..................... B01L 3/5453
73/864.91
(Continued)

FOREIGN PATENT DOCUMENTS

CN 1045563 A 9/1990
CN 101084101 A 12/2007
(Continued)

OTHER PUBLICATIONS

The World Intellectual Property Organization (WIPO) International Search Report for PCT/CN2014/082870 dated Nov. 15, 2014.

*Primary Examiner* — Paul S Hyun
(74) *Attorney, Agent, or Firm* — Anova Law Group, PLLC

(57) ABSTRACT

The present invention relates to a biological sample preservation tube with an identification code, wherein an information element which records the sample information is fused integrally with the bottom wall and/or side walls during molding the preservation tube, the preservation tube is suitable for the preservation of a biological sample at low temperature and can ensure the effectiveness and stability at low temperature; and at the same time also relates to a method for manufacturing the biological sample preservation tube, wherein the preservation tube is molded by a one-step process, without an additional secondary processes for manufacturing the identification code, the method improves the production efficiency, reduces the production cost, employs multi-point symmetrical feeding, and has good quality and stability of the product, so that the method is of great significance as it opens up a new idea for (Continued)

developing and producing the similar product in the industry, especially the small-sized preservation tube with an identification code.

5 Claims, 5 Drawing Sheets

(51) Int. Cl.
    *A61B 10/00*     (2006.01)
    *B01L 3/00*     (2006.01)
    *B29L 31/00*     (2006.01)
    *A61B 17/00*     (2006.01)

(52) U.S. Cl.
    CPC . *A61B 2017/00526* (2013.01); *A61B 2562/08* (2013.01); *B01L 2300/021* (2013.01); *B01L 2300/0851* (2013.01); *B01L 2300/0858* (2013.01); *B29C 2045/14918* (2013.01); *B29L 2031/712* (2013.01); *B29L 2031/753* (2013.01)

(56) References Cited

U.S. PATENT DOCUMENTS

| 2012/0122236 A1* | 5/2012 | Tarpey | G01N 21/8483 |
| | | | 436/501 |
| 2014/0287079 A1* | 9/2014 | Hosokoshiyama | B29C 49/0078 |
| | | | 425/130 |

FOREIGN PATENT DOCUMENTS

| CN | 101254640 A | 9/2008 |
| CN | 101821167 A | 9/2010 |
| CN | 102576502 A | 7/2012 |
| CN | 103521278 A | 1/2014 |
| CN | 203635228 U | 6/2014 |

* cited by examiner

BIOLOGICAL SAMPLE PRESERVATION TUBE WITH IDENTIFICATION CODE AND METHOD FOR MANUFACTURING THE SAME

CROSS-REFERENCES TO RELATED APPLICATIONS

This patent application is a continuation of PCT Patent Application No. PCT/CN2014/082870, filed on Jul. 24, 2014, which claims priority of Chinese Patent Application No. 201310487889.6, filed on Oct. 18, 2013, the entire content of which is incorporated by reference herein.

FIELD OF INVENTION

The present invention relates to a biological sample preservation tube and a method for manufacturing the same, particularly to a biological sample preservation tube with an identification code and a method for manufacturing the same, wherein the effectiveness and stability of the identification code on the biological sample preservation tube at low temperature can be ensured.

BACKGROUND

With the development of life science, the studies and concerns on the interaction among the environment, heredity, and habit of life have become hot spots in the field of science. Especially, in recent years, the initiative translational medicine, synthetic biology, and other new interdisciplines pay more attention on large-scale of collection and preservation of a variety of biological genetic substances, metabolites, environmental samples and the like for study and analysis in the future. After appropriately treating, these samples are preserved in different sizes of tubular containers, such as the small one with a volume of 0.2 ml, the big test tube with a volume of 10 ml or more, herein all of them are referred to as sample preservation tubes.

The sample preservation tubes used in life science are generally preserved at extremely low temperature (such as liquid nitrogen, −196° C.), however, the adhesive used in the conventional label for recording the sample information is usually invalid at such extreme temperature. Therefore, how to ensure the stability of the code on the label at low temperature has become an important issue to be resolved in such sample preservation tube. In order to solve this problem, in the patent U.S. Pat. No. 6,270,728 B1 of Micrometeric Company, US, it is disclosed that the identification code is manufactured on a carrier, and the carrier is fixed to the bottom of the sample cryogenic tube by means of clamping, sticking, etc. In the patent U.S. Pat. No. 6,372,293 B1 of Matrix Company, US, it is disclosed that the two dark and light color layers of coatings with different properties are directly overlaid on the bottom, and then for example, the laser etching is used to remove off the surface coating in accordance with a predetermined pattern, and expose the color of the underlying layer so as to form an identification code with a contrast of dark and light colors. Likewise, in the patent US 2011/0308335 A1 of Nexus Biosystems Company, laser etching is also used to obtain an identification code, the difference from those of Matrix Company is that an opaque coating is applied to the underlying layer on the bottom, and a special transparent coating is overlaid on the surface layer, under a laser irradiation at a specific wavelength, the transparent coating on the top will occur a change in color and form a contrast with the opaque coating on the underlying layer, thereby manufacturing an identification code. In the patent of Q.I.S Company, it is disclosed a method for labeling a data coding matrix on a glassy sample preservation tube, wherein a ceramic coating is directly sprayed on the bottom of the glassy sample preservation tube, then fixed by sintering, thereby forming a firm identification code. In addition, in the patent US 2012/0048827 A1 of Wheaton Company, a special structure is disclosed, in which an element with an identification code can be fixed on the bottom of the sample preservation tube. Likewise, in the patent U.S. Pat. No. 8,282,782 B2, disclosed is a method that an identification code is labeled on a jacket and the jacket is wrapped on the outside of the sample preservation tube, in which not only a two-dimensional code can be labeled on the bottom of the sample preservation tube, but also can a one-dimensional code and a naked eye identifiable numerical coding be labeled on the side wall of the sample preservation tube simultaneously, when the two-dimensional code on the bottom is damaged, the one-dimensional code and the naked eye identifiable numerical coding on the side wall can still provide a sufficient coding identification, thus increasing the coding reliability of the sample preservation tube.

Although a plurality of ways for labeling data coding matrix on the outside of sample preservation tube (bottom or outer side wall) have been disclosed in numerous patents, these processes all require an additional process, in addition to the process for manufacturing the sample preservation tube, to fix the identification code on the tube body of the preservation tube, thereby limiting the efficiency of large-scale production and increasing the production cost.

According to the present disclosure, an in-mold labeling process is a new technology which is popular in the recent decade, wherein the manufactured label is placed in the mold, and the label and the product are integrally combined in the injection molding process. As compared to the traditional labeling process, the in-mold labeling process is very stable under low temperature stringent environment. However, due to the very small volume of the biological sample preservation tube (even as small as 0.2 ml), it is still not found a suitable manner for matching the mold manufacturing and the in-mold labeling, thus limiting the application of the in-mold labeling technology in the field for labeling a biological sample preservation tube.

The disclosed medical monitor mounting systems are directed at solving one or more problems set forth above and other problems.

BRIEF SUMMARY OF THE DISCLOSURE

The objectives of the present invention are to provide a biological sample preservation tube in which an identification code is labeled by an in-mold labeling technology, and to provide a method for manufacturing the biological sample preservation tube and fusing the identification code onto the biological sample preservation tube simultaneously, the method does not require an additional secondary process to fix the information element onto the body of the sample preservation tube, provides a sample preservation tube with high quality and good stability, and at the same time reduces the production cost of the sample preservation tube, and solves the problems in the art that the accurate and high-quality in-mold labeling can hardly been achieved due to the too small size of the sample preservation tube.

In order to achieve the abovementioned objects, the following technical solutions are employed in the present invention: a biological sample preservation tube with an identification code, comprising a tube body, wherein the tube body comprises integrally molded bottom wall and side wall, the bottom wall and/or side wall are integrally fused with the information element in the in-mold labeling process, the information element comprises a core layer and a heat sealing layer, the core layer is provided with an identification code, and the heat sealing layer is transparent and overlaid on the identification code to provide a protective effect. The core layer and the heat sealing layer are integrally molded preferably by means of coating or co-extrusion.

The abovementioned tube body is made of the material which is selected from PP, ABS, PE or PC, but is not limited thereto.

The abovementioned tube body and the core layer are made of the same material, which facilitates to increase the fusion firmness of the tube body and the core layer.

The abovementioned identification code is an optical data coding matrix, which can be read by an optical reading device or naked eyes. The open data coding matrix, such as, one-dimensional bar code Code39 and Code128, or two-dimensional bar code Datamatrix, and the naked eye identifiable numbers or letters are preferred The abovementioned core layer is a thin film layer structure, with a thickness of 70-90 micrometers, preferably, made into the required shape and thickness by means of extrusion, stretching, etc.

As a specific structure, the abovementioned bottom wall is fused with the information element, and the identification code of the information element is a black background-white dot two-dimensional code provided on the core layer.

As another specific structure, both the abovementioned bottom wall and the side wall are fused with a information element, the identification code on the information element comprises a two-dimensional code fused with the bottom wall and a one-dimensional code fused with the side wall, and the two-dimensional code and the one-dimensional code are connected together by a connecting structure.

For better understanding the present invention, the method for manufacturing the abovementioned biological sample preservation tube with the identification code is described in detail below, specially comprising the steps of:

S1. manufacturing the information element: the identification code is printed on the core layer, then the inner surface of the heat sealing layer is overlaid on the core layer, so that the core layer and the heat sealing layer are integrally formed an information element;

S2. cutting the information element: the information element manufactured in step S1 is cut into a size not exceeding that of the position to be fused, the cut information elements are removed off static electricity to avoid them from attaching to each other, then placed on the same support frame as a mold, for taking by a robotic hand;

S3. picking and placing the information element: the information element cut in step S2 is placed in a predetermined position in the mold by the robotic hand, when placing the information element, the side with an identification code is faced away from the inner core, then static electricity is applied to the identification code and/or the information element, due to its characteristics, the identification code and/or the information element is attached onto the mold under the effect of electrostatic field to be temporarily fixed;

S4. mold closing and injection molding: the mold and the inner core are closed, the molten plastic feedstock is injected into the mold via at least two symmetric feed channels from both sides of the mold, each feed channel is reflexed at the point close to a feed inlet, and the feed inlet is pointed to the center position of the bottom wall, so as to produce a biological sample preservation tube with an identification code. Such design is to ensure the produced biological sample preservation tube having a uniform thickness, and avoid the information element from moving its position or curling and deforming when the molten plastic rushing into the mold at a high speed, so as to ensure the high quality of the product.

Among them, the abovementioned feed inlets are an even number, and symmetrically distributed in the mold. The preferred design is that there are two feed inlets, each corresponding to a feed pipeline, and the feed inlet and the feed pipeline are symmetrically arranged; the feed inlets are symmetrically distributed close to the bottom surface of the mold, and are pointed to the bottom center of the biological sample preservation tube to be molded, such design can avoid the information element from rushing away from the predetermined position by the high-pressure feedstock in the in-mold labeling process.

The present invention has the advantages as follows: as the information element which records the sample information is fused integrally with the bottom wall and/or side wall during molding the preservation tube, the biological sample preservation tube of the present invention is suitable for preserving a biological sample at low temperature, and can ensure the effectiveness and stability at low temperature; no additional secondary process is required to manufacture an identification code for the preservation tube, so that the production efficiency is increased, the production cost is reduced, and the quality and stability are good; and the method for manufacturing the biological sample preservation tube of the present invention employs multi-point symmetrical feed, and the feed inlets are pointed to the center position of the bottom wall, so that the method is of great significance as it opens up a new idea for producing the similar product in the industry, especially the small-sized preservation tube with an identification code.

Other aspects of the present disclosure can be understood by those skilled in the art in light of the description, the claims, and the drawings of the present disclosure.

DETAILED DESCRIPTION

Figure 1:
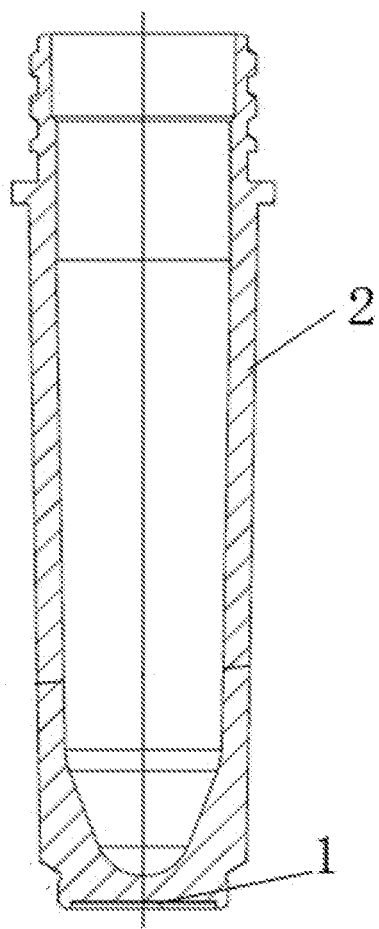
FIG. 1 is a schematic diagram of the cross-sectional structure according to the first example of the biological sample preservation tube of the present invention.

Reference will now be made in detail to exemplary embodiments of the invention, which are illustrated in the accompanying drawings. Wherever possible, the same reference numbers will be used throughout the drawings to refer to the same or like parts. Notation of the reference numerals are as follows: 1. information element, 2. preservation tube, 3. mold, 4. feed pipeline, 5. feed inlet, 6. inner core, and 7. connecting structure.

Example 1

Figure 2:
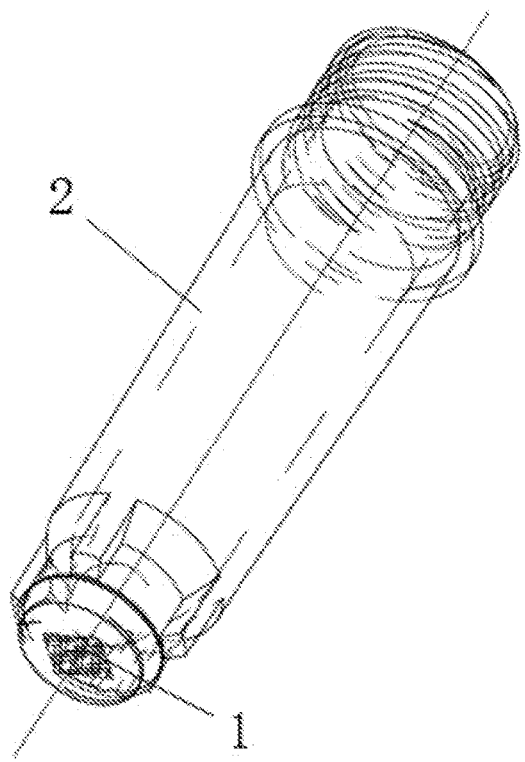
FIG. 2 is a schematic diagram of the perspective structure of the example shown in FIG. 1.
Figure 3:
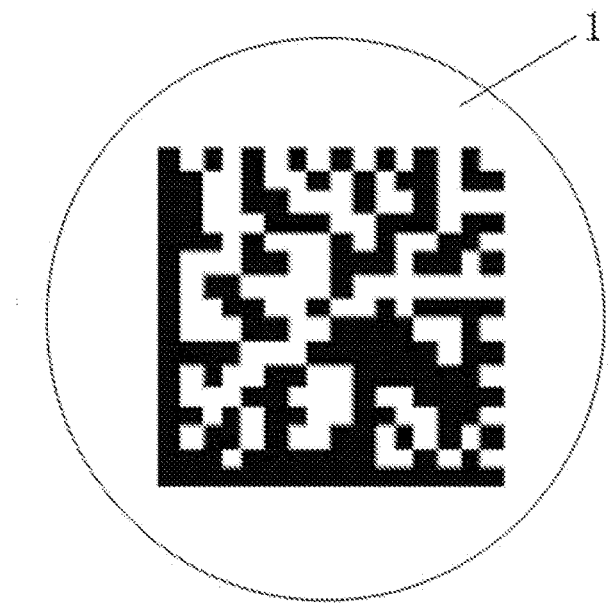
FIG. 3 is a schematic diagram of the information element used in the example as shown in FIG. 1.
Figure 4:
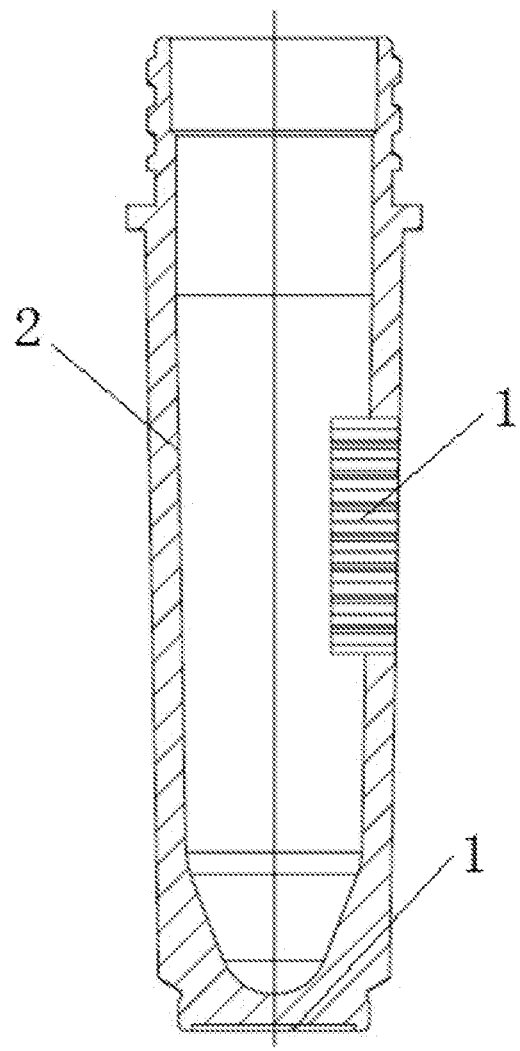
FIG. 4 is a schematic diagram of the cross-sectional structure according to the second example of the biological sample preservation tube of the present invention.
Figure 5:
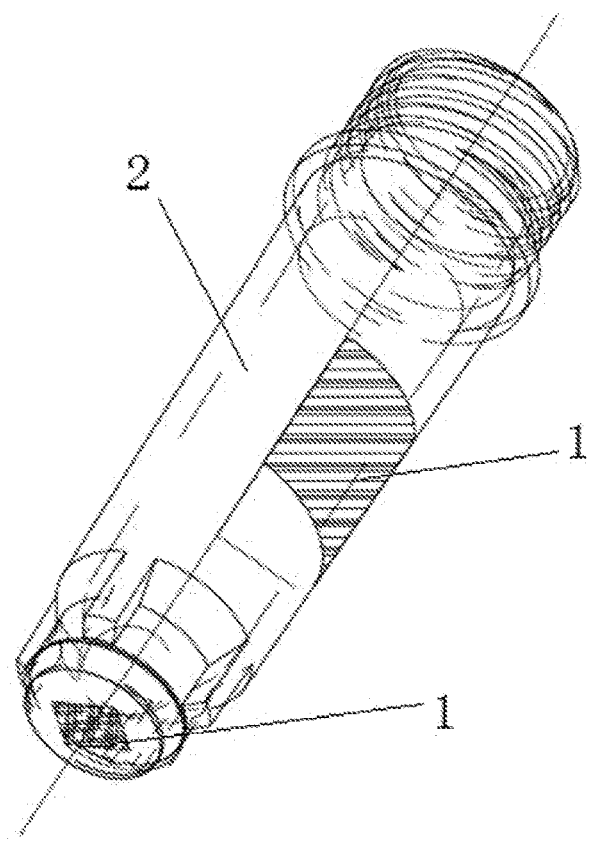
FIG. 5 is a schematic diagram of the perspective structure of the example shown in FIG. 4.

The biological sample preservation tube 2 produced in this example was made of a polypropylene (PP) material so as to have an extremely low temperature tolerance performance, and the core layer of the information element 1 was also made of the same PP material, and the information element 1 was only provided on the bottom wall of the biological sample preservation tube 2, as shown in FIGS. 1-3.

First, the PP material was made into a film of the core layer by means of extrusion, stretching, etc, with a film thickness of 70 to 90 micrometers. A black background-white dot two-dimensional bar code was printed on the core layer, and overlaid a transparent heat-sealing layer so as to protect the two-dimensional bar code, then the manufactured information element 1 was cut so as to obtain a circular information element 1 with a size not exceeding that of the bottom of the tube, and shape similar to that of the bottom of the tube, for use, as shown in FIG. 3.

Figure 7:
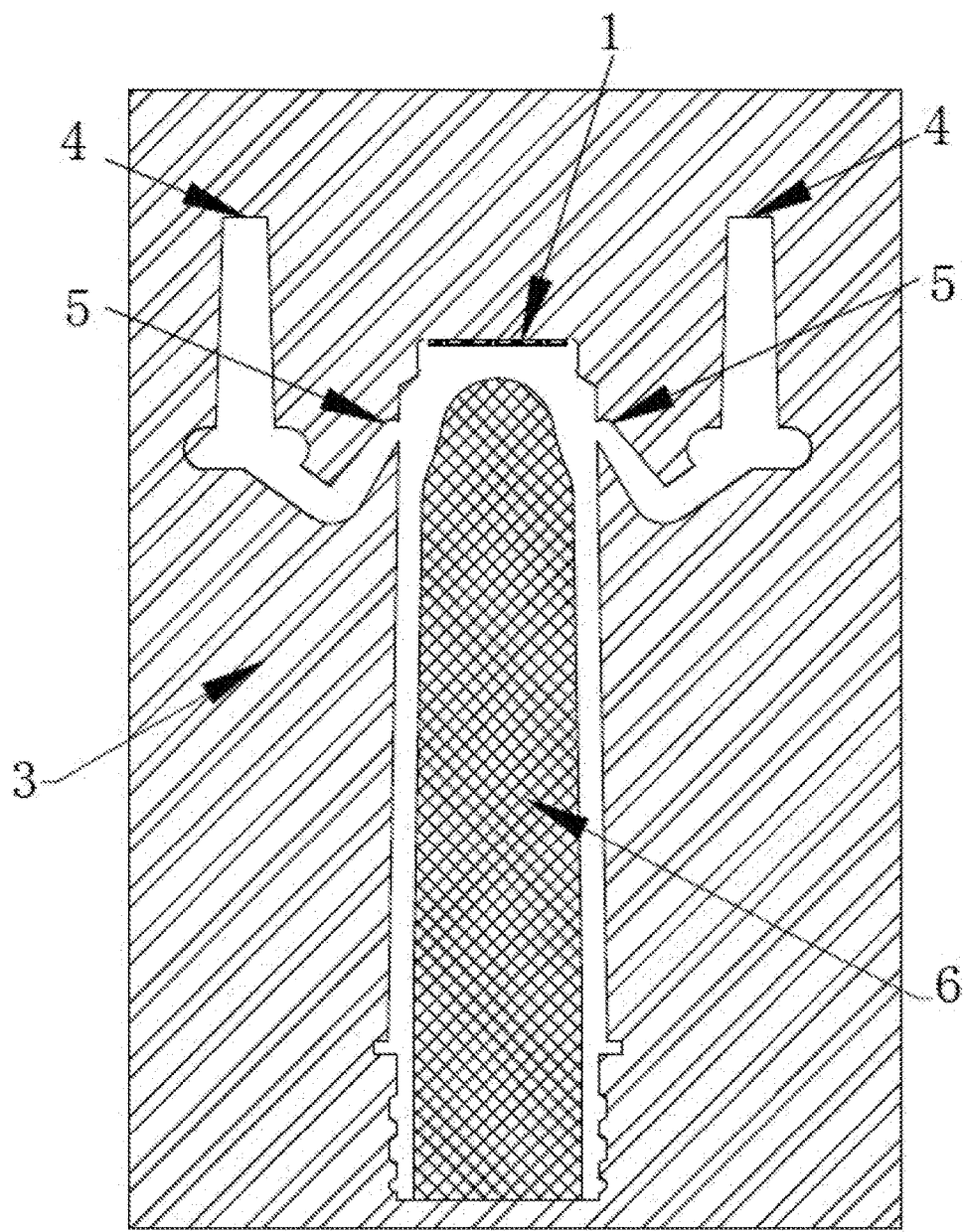
FIG. 7 is a schematic structural diagram of the mold for manufacturing the biological sample preservation tube of the present invention.

In production, the information element 1 was picked up using a special clamp, and put on the bottom wall in the mold 3, with the side having a code facing toward the outer wall of the mold cavity, and facing away from the inner core, as shown in FIG. 7, and static electricity was applied to the information element 1, the information element 1 with static electricity was attached to the mold 3 so as to prevent the position moving in the mold closing process. The mold 3 and the inner core 6 were closed, the molten PP feedstock was introduced into the mold 3 via a symmetrically arranged feed pipeline 4, the feed pipeline 4 was reflexed at the point close to the feed inlet 5, the connecting line between the reflexed feed pipeline 4 and the feed inlet 5 was extended to point to the bottom center of the mold 3, i.e., the center position of the information element 1, which was the center position of the e bottom wall of the biological sample preservation tube 2 to be molded, such design allowed that the information element 1 was compressed by the molten feedstock immediately after it was introduced into the mold cavity, thereby ensuring the information element 1 not deviating from its original position. A plurality of feed inlets 5 were symmetrically designed to ensure the produced biological sample preservation tube 2 having a uniform thickness, and avoid the information element 1 from moving its position, or curling and deforming by the rushed molten plastic during production, thereby ensuring the high quality of the product.

Example 2

Figure 6:
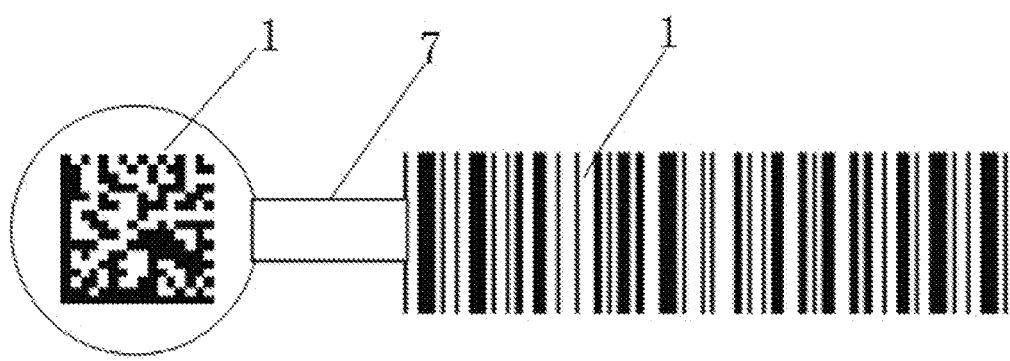
FIG. 6 is a schematic diagram of the information element used in the example as shown in FIG. 4.

The biological sample preservation tube 2 in this example was made of a polypropylene material, with a two-dimensional code provided on the bottom wall, and a one-dimensional code provided on the side wall. First, the information element 1 was manufactured as shown in FIG. 6, the core layer was made of a polypropylene material, and the circular two-dimensional code and the rectangular one-dimensional code, both representing the same information, were connected together by a connecting structure 7. In production, this method was substantially the same as those in example 1, except that the one-dimensional code part was electrostatically attached onto the side wall of the mold 3, fed, and molded the biological sample preservation tube 2 with the identification code on both the bottom wall and the side wall.

Example 3

This example was substantially the same as Example 1, except that the biological sample preservation tube 2 in this example was made of a polyethylene (PE) material, and the core layer of the information element was also made of the PE material.

Example 4

This example was substantially the same as Example 2, except that the biological sample preservation tube 2 in this example was made of a PC material, and the core layer of the information element was made of the PC material.

Example 5

This example was substantially the same as Example 4, except that the sample preservation tube 2 was made of an ABS material, and the core layer of the information element was made of the ABS material, but the information element was only fused onto the bottom wall.

Example 6

This example was substantially the same as Example 3, except that the information element was only fused onto the sidewall, and the information element was rectangular.

In summary, the biological sample preservation tube 2, the information element 1 and the tube body produced according to the method of the present invention are obtained by high temperature fusion of the same materials, and the molecules are inter-crosslinked to form an integral structure, without bonding with an adhesive, therefore the good effectiveness and stability can also be maintained even at low temperature. As compared to the process for manufacturing a sample preservation tube with a two-dimensional code in the art, the process in the present invention can produce the sample preservation tube 2 and at the same time fuse the information element 1, which can not only save the manufacturing process, improve the efficiency and reduce the production cost, but also ensure the high quality of the product.

The basic principles, the main features and advantages of the present invention are shown and described above. It should be clear for those skilled in the art that the examples are not intended to limit the present invention in any way, all of the technical solutions obtained by using the equivalent replacement or equivalent alternative should fall within the scope of the present invention.

What is claimed is:
1. A method for making a biological sample preservation tube with an identification code, comprising:
  manufacturing an information element, including:
    printing the identification code on a core layer;
    overlaying a heat sealing layer on the identification code of the core layer; and
    forming the information element by integrating the core layer and the heat sealing layer;
  cutting the information element, including:
    cutting the information element into a size not exceeding that of a position to be fused, and each cut information element is removed off static electricity to avoid attaching to each other; and placing the cut information element on a same support frame as a mold, for being taken by a robotic hand;

picking and placing the information element, including:
placing the cut information element on a predetermined position in the mold by the robotic hand, with a side of the cut information element having the identification code facing away from an inner core attached to an outer wall of a mold cavity;
applying static electricity on the cut information element such that the cut information element is attached onto the mold under the effect of the electrostatic field for temporary fixation; and performing mold closing and injection molding to form the biological sample preservation tube, including:
injecting molten plastic feedstock into the mold via at least two symmetric feed channels from both sides of the mold, each feed channel being reflexed at a point close to a plurality of feed inlets pointing to a center position of a bottom side of the mold, the at least two symmetric feed channels introducing the molten plastic feedstock into the mold.

2. The method according to claim 1, wherein the feed inlets are an even number, and are symmetrically distributed in the mold.

3. The method according to claim 1, wherein the core layer is made into a required thickness by means of extrusion or stretching, and the core layer and the heat sealing layer are integrally molded by means of coating or co-extrusion.

4. The method according to claim 1, wherein placing the cut information element on the predetermined position in the mold by the robotic hand comprises:
placing a first cut information element on both a bottom position and placing a second cut information element on a side wall position in the mold by the robotic hand.

5. The method according to claim 1, wherein performing mold closing and injection molding to form the biological sample preservation tube comprises:
injecting molten plastic feedstock into the mold to surround another side of the cut information element without the identification code and a side surface of the information element.

* * * * *